United States Patent
Schwarz et al.

(10) Patent No.: US 9,446,258 B1
(45) Date of Patent: Sep. 20, 2016

(54) DEVICE AND METHOD FOR CONTACTLESS SKIN TREATMENT

(71) Applicant: BTL HOLDINGS LIMITED, Limassol (CY)

(72) Inventors: Tomáš Schwarz, Prague (CZ); Jan Žárský, Framington, MA (US)

(73) Assignee: BTL Holdings Limited, Limassol (CY)

( * ) Notice: Subject to any disclaimer, the term of this patent is extended or adjusted under 35 U.S.C. 154(b) by 0 days.

(21) Appl. No.: 14/700,349

(22) Filed: Apr. 30, 2015

Related U.S. Application Data

(63) Continuation of application No. 14/637,930, filed on Mar. 4, 2015.

(51) Int. Cl.
 *A61N 1/00* (2006.01)
 *A61N 1/40* (2006.01)

(52) U.S. Cl.
 CPC .................................. *A61N 1/403* (2013.01)

(58) Field of Classification Search
 CPC .. A61B 18/14; A61B 18/18; A61B 18/1815; A61B 2018/00464; A61B 2018/00458; A61B 2018/00452; A61B 2018/147; A61B 2018/00005; A61B 2018/00017; A61B 1/403; A61B 5/025
 See application file for complete search history.

(56) References Cited

U.S. PATENT DOCUMENTS

| | | | |
|---|---|---|---|
| 866,376 A | 9/1907 | Meade | |
| 3,854,968 A | 12/1974 | Minnick | |
| 4,255,398 A | 3/1981 | Tanaka | |
| 4,256,500 A | 3/1981 | Turpin, Jr. | |
| 4,256,504 A | 3/1981 | Dunstan, Jr. | |
| 4,312,364 A | 1/1982 | Convert et al. | |
| 5,118,219 A | 6/1992 | Walker, Jr. | |
| 5,295,955 A | 3/1994 | Rosen | |
| 5,433,740 A * | 7/1995 | Yamaguchi | A61N 1/403 607/102 |
| 5,507,790 A | 4/1996 | Weiss | |
| 5,660,836 A | 8/1997 | Knowlton | |
| 5,755,753 A | 5/1998 | Knowlton | |
| 5,919,219 A | 7/1999 | Knowlton | |

(Continued)

FOREIGN PATENT DOCUMENTS

| | | |
|---|---|---|
| EP | 1158919 A1 | 12/2001 |
| GB | 2265916 | 10/1993 |
| WO | 97-39054 | 10/1997 |
| WO | 0053113 | 9/2000 |

OTHER PUBLICATIONS

European Patent Office, extended European search report in EP Patent Application No. 12849633.8 dated Jun. 15, 2015.

Nel, P., et al., "Non-destructive micro-X-ray diffraction analysis of painted artefacts: Determination of detection limits for the chromium oxide-zinc oxide matris", Nuclear Instruments and Methods in Physics Research B, 251, pp. 489-495 (2006).

(Continued)

*Primary Examiner* — Kaitlyn Smith
(74) *Attorney, Agent, or Firm* — Kenneth H. Ohriner; Perkins Coie LLP

(57) ABSTRACT

Devices and methods for contactless skin treatment use feedback power control for non-invasive treatment of skin and human tissue. Electromagnetic energy heats skin or tissue. A feedback system measures an output physical quantity before the output of electromagnetic waves from the device into the patient. Alternatively the feedback system scans values of a physical quantity on or near the patient. The devices and methods allow for delivering the optimum amount of energy to the patient while reducing the thermal load of the device.

26 Claims, 1 Drawing Sheet

(56) References Cited

U.S. PATENT DOCUMENTS

| | | | |
|---|---|---|---|
| 6,008,653 A | 12/1999 | Popovic et al. | |
| 6,047,215 A * | 4/2000 | McClure | A61B 18/1492 607/101 |
| 6,208,903 B1 | 3/2001 | Richards | |
| 6,241,753 B1 | 6/2001 | Knowlton | |
| 6,334,074 B1 * | 12/2001 | Spertell | A61N 5/04 606/31 |
| 6,377,855 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,406,474 B1 | 6/2002 | Neuberger et al. | |
| 6,413,255 B1 | 7/2002 | Stern | |
| 6,511,475 B1 | 1/2003 | Altshuler et al. | |
| 6,641,658 B1 | 11/2003 | Dubey | |
| 6,662,054 B2 | 12/2003 | Kreindel et al. | |
| 6,725,095 B2 | 4/2004 | Fenn et al. | |
| 6,749,624 B2 | 6/2004 | Knowlton | |
| 6,766,202 B2 | 7/2004 | Underwood et al. | |
| 6,858,000 B1 | 2/2005 | Naraikin et al. | |
| 7,006,874 B2 | 2/2006 | Knowlton et al. | |
| 7,189,230 B2 | 3/2007 | Knowlton | |
| 7,229,436 B2 | 6/2007 | Stern et al. | |
| 7,267,675 B2 | 9/2007 | Stern et al. | |
| 7,630,774 B2 * | 12/2009 | Karni | A61B 18/042 600/10 |
| 7,643,883 B2 * | 1/2010 | Kreindel | A61B 18/14 607/101 |
| 8,548,599 B2 * | 10/2013 | Zarsky | A61B 18/18 607/101 |
| 2003/0187488 A1 | 10/2003 | Kreindel et al. | |
| 2004/0003757 A1 | 1/2004 | Chern Lin et al. | |
| 2004/0015163 A1 * | 1/2004 | Buysse | A61B 18/1206 606/34 |
| 2004/0040474 A1 | 3/2004 | Perez-Pena et al. | |
| 2004/0044385 A1 | 3/2004 | Fenn et al. | |
| 2005/0182462 A1 | 8/2005 | Chornenky et al. | |
| 2005/0203504 A1 * | 9/2005 | Wham | A61B 18/1442 606/34 |
| 2006/0036300 A1 | 2/2006 | Kreindel | |
| 2006/0094988 A1 | 5/2006 | Tosaya et al. | |
| 2006/0173518 A1 | 8/2006 | Kreindel | |
| 2006/0195168 A1 * | 8/2006 | Dunbar | A61F 7/007 607/108 |
| 2006/0206180 A1 * | 9/2006 | Alcidi | A61N 1/06 607/102 |
| 2006/0265034 A1 | 11/2006 | Aknine et al. | |
| 2007/0038206 A1 | 2/2007 | Altshuler et al. | |
| 2007/0106349 A1 | 5/2007 | Karni et al. | |
| 2007/0135811 A1 * | 6/2007 | Hooven | A61B 18/1445 606/41 |
| 2007/0173805 A1 * | 7/2007 | Weinberg | A61B 18/1206 606/34 |
| 2007/0244530 A1 * | 10/2007 | Ren | A61N 5/02 607/101 |
| 2007/0270795 A1 * | 11/2007 | Francischelli | A61B 18/1206 606/41 |
| 2007/0282318 A1 | 12/2007 | Spooner et al. | |
| 2008/0009885 A1 | 1/2008 | Del Giglio | |
| 2008/0082094 A1 * | 4/2008 | McPherson | A61B 18/1206 606/34 |
| 2008/0183167 A1 | 7/2008 | Britva et al. | |
| 2008/0183251 A1 * | 7/2008 | Azar | A61B 18/18 607/101 |
| 2008/0255572 A1 * | 10/2008 | Zeller | A61B 17/1617 606/96 |
| 2008/0287948 A1 * | 11/2008 | Newton | A61B 18/1206 606/50 |
| 2009/0024193 A1 | 1/2009 | Altshuler et al. | |
| 2009/0125013 A1 | 5/2009 | Sypniewski et al. | |
| 2009/0221938 A1 | 9/2009 | Rosenberg et al. | |
| 2009/0306648 A1 * | 12/2009 | Podhajsky | A61B 18/1206 606/38 |
| 2010/0087816 A1 * | 4/2010 | Roy | A61B 18/1445 606/48 |
| 2010/0100092 A1 | 4/2010 | Turner et al. | |
| 2010/0228250 A1 * | 9/2010 | Brogna | A61B 18/1445 606/45 |
| 2010/0286673 A1 | 11/2010 | Altshuler et al. | |
| 2010/0286691 A1 * | 11/2010 | Kerr | A61B 18/1206 606/51 |
| 2011/0112520 A1 | 5/2011 | Michael | |
| 2011/0130750 A1 | 6/2011 | Ormsby et al. | |
| 2011/0202058 A1 * | 8/2011 | Eder | A61B 18/1442 606/50 |
| 2011/0245900 A1 * | 10/2011 | Turner | A61N 1/403 607/100 |
| 2011/0295187 A1 | 12/2011 | Shanks et al. | |
| 2012/0010609 A1 | 1/2012 | Deem et al. | |
| 2012/0016359 A1 * | 1/2012 | Podhajsky | A61B 18/1206 606/34 |
| 2012/0022622 A1 | 1/2012 | Johnson et al. | |
| 2012/0078141 A1 | 3/2012 | Knowlton | |
| 2012/0226272 A1 * | 9/2012 | Chernov | A61B 5/0295 606/34 |
| 2013/0123629 A1 | 5/2013 | Rosenberg et al. | |
| 2013/0123765 A1 * | 5/2013 | Zarsky | A61N 1/40 606/13 |
| 2013/0144280 A1 * | 6/2013 | Eckhouse | A45D 26/00 606/9 |
| 2014/0249609 A1 * | 9/2014 | Zarsky | A61N 1/40 607/102 |
| 2014/0257071 A1 * | 9/2014 | Curran | A61B 5/063 600/374 |
| 2015/0238248 A1 * | 8/2015 | Thompson | A61B 18/1402 606/50 |
| 2015/0238771 A1 * | 8/2015 | Zarsk | A61N 1/40 607/102 |
| 2016/0066977 A1 * | 3/2016 | Neal, II | C12N 13/00 606/34 |

OTHER PUBLICATIONS

Abo-El-Enein, S.A., et al., "Blended Cements Containing Cement Kiln Dust", Silicates Industries, vol. 59, No. 9-10, pp. 265-269 (1994).

Hawkins, Peter et al., "The Use of Limestone in Portland Cement: A State-of-the-Art Review", Engineering Bulletin 227, Portland Cement Association, Skokie, Illinois, 41 pages (2003).

Ravindrarajah, R.S., "Use of cement kiln dust in concrete", The International Journal of Cement Composites and Lightweight Concrete, vol. 4, No. 2, pp. 95-102 (May 1982).

Kitahara,Shinichi et al., "Precision and detection limit of quality test for amorphous drug in powder x-ray diffractometry". International Journal of Pharmaceutics, 283, pp. 63-69 (2004).

Cody, A.M, et al., "The effects of chemical environment on the nucleation, growth, and stability of ettringite". Cement and Concrete Research, 34, pp. 869-881 (2004).

United States Patent and Trademark Office, Non-final Office Action issued in U.S. Appl. No. 13/297,608 (Feb. 16, 2012).

United States Patent and Trademark Office, Final Office Action issued in U.S. Appl. No. 13/297,608 (May 21, 2012).

United States Patent and Trademark Office, Non-final Office Action issued in U.S. Appl. No. 13/297,608 (Aug. 16, 2012).

United States Patent and Trademark Office, Final Office Action issued in U.S. Appl. No. 13/297,608 (Mar. 20, 2013).

United States Patent and Trademark Office, Non-final Office Action issued in U.S. Appl. No. 13/297,934 (Feb. 17, 2012).

United States Patent and Trademark Office, Final Office Action issued in U.S. Appl. No. 13/297,934 (May 21, 2012).

United States Patent and Trademark Office, Decision on Appeal issued in U.S. Appl. No. 13/297,934 (Oct. 29, 2015).

Korean Intellectual Property Office, The International Search Report and the Written Opinion issued in PCT International Application No. PCT/US2012/064942 (Mar. 15, 2013).

Korean Intellectual Property Office, The International Search Report and The Written Opinion issued in International application No. PCT/US2016/019711 (Jun. 7, 2016).

* cited by examiner

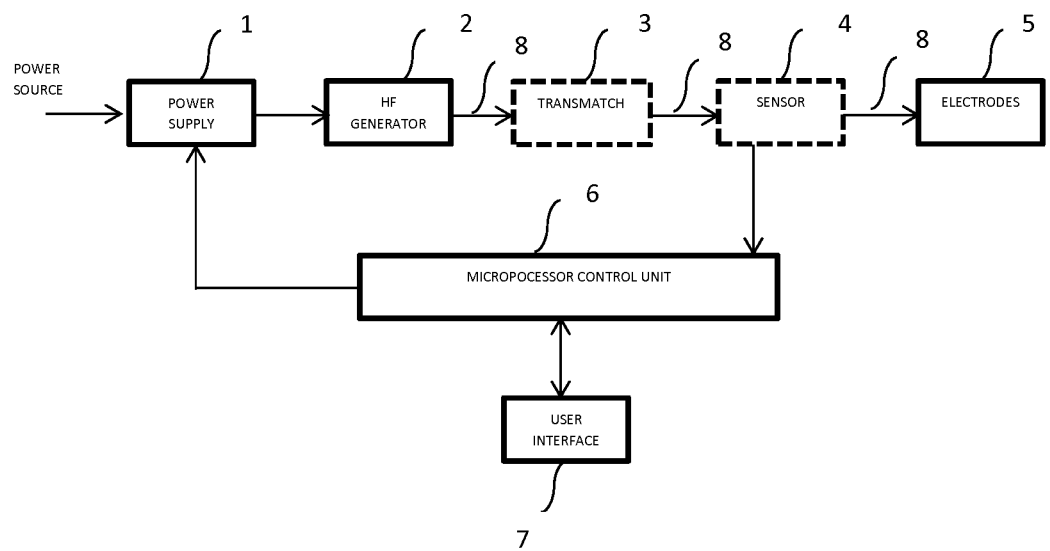

DEVICE AND METHOD FOR CONTACTLESS SKIN TREATMENT

PRIORITY CLAIM

This Application is a Continuation of U.S. patent application Ser. No. 14/637,930, filed Mar. 4, 2015, and now pending.

BACKGROUND OF THE INVENTION

Human skin consists of three basic layers: the epidermis, the dermis and the hypodermis. The outer layer of skin is the epidermis. Epidermis is the thinnest of the layers and contains mainly stratified squamous epithelium of which the outer side keratinizes and ensures coverage. The inner side contains a pigment. The middle layer of skin is the dermis. Dermis consists mainly of the collagen, elastic and reticular fibers. The bottom layer of skin is the hypodermis. The hypodermis is formed mainly by blood vessels, lymphatic vessels, nerve fibers, fibroblasts and in particular adipocytes.

Increases in average life expectancy, obesity, unhealthy lifestyles, genetic predispositions and other factors may cause aesthetically undesirable appearance of the skin. The undesirable appearance of the skin may manifest itself by excessive volume of fat, cellulite, skin laxity, loss of elasticity, loss of firmness, etc. The undesirable appearance is caused mainly by the excessive volume of fat cells, weakness and/or break down of collagen, elastin fibers or other known reasons.

Aesthetic devices delivering an electromagnetic energy have recently been developed and various invasive and contact approaches solving undesirable skin appearance are known. However invasive methods require long recovery time and place high time and skill demands on practitioners. They also involve strict requirements for a sterile environment and biocompatibility. Invasive treatments can be painful and traumatic. Moreover there is always risk of infection and inflammation of the treated tissue.

Non-invasive methods which still require contact with the patient also must fulfill high sterility and biocompatibility requirements. The operator of a contact device must disinfect or replace an individual contact part of the applicator before or during the application, which consumes time of the operator.

Non-contact treatment eliminates these disadvantages since it reduces the time required for disinfection, and replacement of an individual contact part or manipulation along the treated area. Since the devices do not contact with the patient there is no need for biocompatible materials.

Non-contact radiofrequency therapy can be used for reduction of volume and number of fat cells in the hypodermis, removal of cellulite, body contouring, neoelastogenesis and neocollagenesis. Methods of these therapies are described for example in US patent application number 2014/0249609, incorporated herein by reference.

However, engineering challenges remain in trying to optimize the amount of energy delivered to the skin of the patient during contactless radio frequency therapy. Current devices for contactless radiofrequency therapy present the values measured at the HF generator as the real output values which are directed to patient, and calculate from these values the energy delivered during therapy.

However, a considerable amount of RF energy is unintentionally converted to other forms of energy in the devices for contactless skin treatment, due to parasitic effects, transformation losses, resistivity of various conductive materials, etc., which limits the amount of output energy.

The actual therapeutic energy delivered to the patient varies depending on the impedance of the patient and distance between patient and the radiofrequency electrode. Since the patient is not in direct contact with a source of RF signal, the distance between patient and the radio frequency electrode during the time therapy is changing. This may be caused either by biological rhythms such as breathing and heartbeat which cause movements of the treated tissue or movements during the duration of therapy. The therapeutic energy delivered may be insufficient due to low electrical resistance of some patients, and distance changes leading to creation of electric potential in thousands of Volts on each symmetrical branch of the non-contact device.

Accordingly, there is need for improvement of the devices for contactless skin treatment so as to control the input power in order to obtain a continuous heating of the target skin and human tissue and to continuously deliver an optimum amount of energy into the skin of the patient without causing any injury to the upper or inner layer of the skin.

SUMMARY OF THE INVENTION

Devices and methods for skin and human tissue therapy use non-invasive and non-contact application of electromagnetic waves, for example in aesthetic medicine. The input power for generating the electromagnetic waves is regulated depending on measured values of at least one physical quantity (such as voltage, current or phase) inside the device or values of one or more physical quantity measured on or near the patient. Via feedback power control, the present devices and methods provide for controlled and continuous delivery of more optimum amounts of energy into the patient and for overheating protection.

An electromagnetic field is generated at frequency in the range of 1 MHz to 100 GHz in a system having a power supply, a high frequency generator and one or more electrodes. A transmatch may optionally be used to improve the power transfer by impedance matching. The transmatch may be placed between the high frequency generator and the at least one electrode.

The high frequency generator generates a signal which further goes to transmatch. The transmatch matches impedance to avoid formation of standing waves along the transmission cable. Afterwards the radio frequency signal is supplied to the at least one electrode. The contactless skin treatment device behaves as a symmetrical voltage power supply.

In order to ensure continuous heating of selected tissue with the optimal energy, the values of at least one physical quantity between the power supply and the electrode are measured. The measured values may be subsequently sent to a control unit or directly to the power supply, which adjusts the input power based on the measured values. Similarly, it is possible to forward only the information about exceeding preset threshold value and accordingly adjust the input power.

Alternatively, the input power is adjusted based on values of at least one built-in or external sensor which measure at least one of the following parameters: temperature, distance between the electrode and the patient, impedance, electric field intensity.

BRIEF DESCRIPTION OF DRAWINGS

FIG. 1 is a block diagram of an apparatus for contactless skin and human tissue treatment with feedback control

GLOSSARY

In the context of the present disclosure, unless otherwise stated:

the "input value" means values of physical quantity before the input to the high frequency generator.

the "output value" means values of physical quantity after the output of the high frequency generator.

the "input power" means energy which inputs to high frequency generator.

the "output power" means energy which outputs the device and is directed to the patient.

DETAILED DESCRIPTION

FIG. 1 depicts a block diagram of a device for contactless treatment of skin and subcutaneous tissue with feedback control of the input power. The device may include a power supply 1, an HF generator 2 and at least one electrode 5. The power supply 1 is connected to power source. The input power of the generated signal exceeds 40 W, and more preferably 80 W. The HF generator 2 may generate an electromagnetic field in the range of 1 MHz to 100 of GHz or optionally other frequencies as well. The 6.78, 13.56, 27.12 and 40.68 MHz; 2.45, 5.80 GHz and all other ISM bands avoid creating radio interference, as these frequencies are exclusively assigned as free or open frequencies.

The output signal from HF generator 2 is subsequently conducted to the electrodes 5, which may be positioned above the surface of the skin or applied on dielectric or insulating, non-conductive material which is in contact with the skin surface. The device for contactless skin treatment delivering RF energy into the patient is constructed as a symmetrical voltage power supply.

One or more sensors 4 are located between the HF generator 2 and at the least one electrode 5 to measure the values of at least one physical quantity, e.g. voltage, current or phase shift between physical quantities.

A transmatch 3 may optionally be connected by transmission cable to the HF generator 2. The transmatch 3 adapts the signal from the RF generator 2 and based on reflection coefficient, measured for example by SWR meter, matches the impedance so as to optimize the power transfer and minimize the reflected signal load. Transmatch 3 is designed to withstand the high power load by using appropriate electromechanical components as is known in the art.

The output signal from transmatch 3 is provided to the electrodes 5 by transmission cables where parasitic effects might occur. The undesirable parasitic effects are caused mainly by internal capacitance of the transmission cables. The parasitic capacitance is intensified by proximity of transmission cables, proximity with other conductors or high frequency signals. Parasitic effects cause reduction of the output power and distort the values measured by the sensor 4.

Significant reduction of parasitic capacitance can be achieved by its material composition and shading of the transmission cables 8. For example, the parasitic capacitance in the transmission cables is reduced or eliminated by using an electric cable with an outer cylindrical conductor and an internal conductor, where the space between them is filled with dielectric. Consequently, it is possible to measure values of at least one physical quantity inside the device more accurately, which allows the actual power delivered to the patient during therapy to be determined.

As shown in FIG. 1 the power supply 1, HF generator 2, transmatch 3 and sensor 4 can be communicatively coupled by microprocessor control unit 6. The microprocessor control unit 6 can provide communication with a user interface 7, which may be a touch screen on the device display.

The contactless device for treatment of the skin and human tissue by radio waves causes controlled heating of the designated areas on the patient. Based on the settings of a treatment device, for example as described in U.S. Patent Publication No. 2014/0249609, the radio waves cause selective heating of the dermis and/or the hypodermis. The controlled heating may lead to remodeling and/or downsizing of a volume of lipid-rich cells and/or remodeling of collagen tissue and/or remodeling of elastic fibers.

However the average impedance of the patient and treatment electrode changes during therapy due to reasons discussed below, which may cause inconsistency in the treatment. The impedance of the patient and treatment electrode can be compared to the impedance of a series circuit consisting of capacitor and resistor. Typical capacitance values ranges about 0.1-100 pF and resistance about 0.1-100 Ohms.

Since the patient is not in direct contact with the source of RF signal, the distance between patient and at least one electrode during the therapy permanently changes. The space between skin of the patient and at least one electrode is occupied by air gap or highly air permeable material. The distance between electrode and patient changes due to movements of the patient and either by biological rhythms such as breathing and heartbeat, which cause vibrations or movements of the treated tissue. Small movements and displacements during the therapy may cause impedance changes and the signal is not tuned for the whole time of the therapy. Therefore the output energy directed to the patient and absorbed by the patient may vary during the therapy.

The actual impedance depends besides the above mentioned factors and also on the shape and disposition of the patient and the amount of adipose tissue. In order to achieve optimal heating of treated skin or subcutaneous tissue in a patient with low resistance, it is necessary to increase the supplied power. The capacitance however causes formation of undesirable high voltage. The voltage can arise to about few kV in this area. Excessive voltages influence the quality of treatment process and may lead to inconsistency of treatment, with variable amounts of energy consumed in the epidermis layer. High voltage may also cause interference nearby electrical equipment.

To overcome these treatment irregularities, in one embodiment the sensor 4 measures the output values of at least one physical quantity (e.g. voltage, current) or phase shift between the physical quantity. In the case of using more than one electrode the sensor 4 may measure the values between different branches of the symmetrical signal cables leading to each electrode. The closer to the electrode the sensor is, the more precise the values can be measured.

However when the sensor 4 is placed near the electrode, the values can be out of scale of common measuring devices, since the output values can reach several kV. Therefore the sensor 4 may optionally be placed closely behind the transmatch 3. The values measured in this part are proportional to the values which are located close to the electrode of the device and are in the range from tens to several hundreds of Volts.

In another embodiment a look-up-table or a correction function can be used for determination of the output values of at least one physical quantity even if the values are measured in any part of the device. The look-up-table can be also used for determination of the output power delivered into the patient. In a similar way it is possible to determine the output power delivered into the patient by a correction function which corresponds to the transmission characteristics of the device e.g. $y=f(x)$, where input x represents the measured value of physical quantity inside the device. Thus by determination of the transmission characteristics it is possible to place the sensor 4 anywhere behind the transmatch so as to measure the output value and calculate the output power which is delivered into the patient.

The actual power delivered to the patient at a given time may be calculated according to the formula $P=U \cdot I \cdot \cos \phi$. Where the U is voltage output value, I is current output value, $\cos \phi$ is a phase shift between voltage and current. Summarization of such calculations may also provide the operator the true energy delivered into the patient during the therapy.

The measured values may be monitored and evaluated even by the sensor itself or by microprocessor control unit 6, which is electrically connected to the sensor 4. If the measured value exceeds a predetermined limit, a feedback signal is sent to the power supply 1 or HF generator 2 to adjust the input power. The signal may include information about exceeding a threshold both qualitative (e.g. yes/no) as well as the quantitative value (e.g. a real value). The signal from sensor 4 can be transmitted as optical information by e.g. optical fiber, so as to eliminate the effects of electromagnetic fields on the transmitted signal.

A method for contactless skin and human treatment starts by gradually increasing input power. The initial input power may be, for example 10 W, and consequently can be increased in predetermined intervals by an additional e.g. 10 W up to the maximum input power for a given therapy. Similarly, the input power can be added continuously. The size of the initial input power, the abrupt increase or rate of continuous increment can differ depending on the kind of therapy.

The input power is gradually increased until the sensor 4 measuring the output values measures an output value greater than the threshold. When the measured values exceed the threshold, the input power is reduced to either the last increment or by a value equal to the amount by which the last measured value exceeds the threshold. The threshold value of the output quantity can be adjusted based on type of therapy.

Since the impedance of the patient is dependent on any change in the distance between the electrode and patient's skin, the system is advantageously responsive to such change. Sampling frequency measurements of the output values of at least one physical quantity should be higher than 0.01 Hz.

The duration of therapy may be influenced by the calculated output power. As an example there may be a predetermined range of the output power for a specific kind of therapy. Time of therapy spent within the predetermined range will be counted into the real time of therapy. Therefore the therapies will be more precise, since the low/high powers will not be included into the treatment time.

According to the yet another embodiment the device for contactless skin and human tissue treatment is in communication with the sensor measuring the electric field intensity. Based on values measured by electric field intensity sensor the input power is adjusted. Communication links can be both wired and wireless. The sensor measuring the electric field intensity can be placed in close proximity to the skin of the patient or directly on the skin, or it can be built into the device or be an external device. If electric field intensity exceeds a predefined threshold, the input power is reduced to either by last increment or by a value equal to the amount by which the last measured value exceeds the threshold.

The skin temperature of the patient may optionally be measured, with input power adjusted based on a measured skin temperature. Optimal skin surface temperature during treatment is between 38° C.-48° C., preferably between 41° C.-44° C. A sensor measuring the temperature of the skin of the patient can be placed in close proximity to the skin of the patient or directly on the skin. If the skin temperature exceeds a predefined threshold, the input power is reduced either by the last increment or by or by a value equal to the amount by which the last measured value exceeds the threshold. Similarly, it is possible to measure the temperature of the skin and/or human tissue by contactless methods as in e.g. WO2014114433, incorporated herein by reference. These may be contact or contactless or invasive method for obtaining detailed information about the temperature in the deep layers. A sensor measuring the temperature of the patient can be built-in or external device.

A distance sensor can measure the distance between the at least one electrode and patient. Based on the measured distance value, input power may be adjusted instantaneously. Optimal distance between electrode and patient varies depending on treatment frequency of radio wave, treated area, impedance, and time duration. The optimal distance may vary over a few tenths of a centimeter. If the distance exceeds a predefined threshold, the input power is reduced at either by last increment or by or by a value equal to the amount by which the last measured value exceeds the threshold. A sensor measuring the distance between the at least one electrode and patient can be built-in or an external device.

Alternatively a system may control the input power according to the received impedance values of the patient. A sensor measuring the impedance of the patient can be built-in or an external device.

The invention claimed is:

1. A device for contactless skin treatment by electromagnetic waves, comprising:
   a power supply electrically connected to a high frequency generator and at least two electrodes;
   a sensor between the power supply and the at least two electrodes for measuring values of at least one physical quantity between different branches of symmetrical signal cables leading to each electrode and where input power to at least one electrode is adjusted based on the measured values.

2. The device according to claim 1 having a transmatch between the high frequency generator and the sensor.

3. The device of claim 2 where the sensor is connected to the at least two electrodes via a cable and measures the values of the at least one physical quantity between the transmatch and the at least two electrodes.

4. The device according to claim 1 wherein input power to the electrodes is adjusted continuously or incrementally based on the measured values.

5. The device of claim 1 where electromagnetic waves cause heating of the skin.

6. The device according to claim 5 where electromagnetic waves cause selective heating of dermis and/or hypodermis.

7. The device of claim 5 where the heating causes remodeling and/or downsizing of a volume of lipid-rich cells and/or remodeling of collagen tissue and/or remodeling of elastic fibers.

8. The device of claim 1 where the measured physical quantity is transformed into optical information.

9. The device of claim 1 further including a control unit electrically connected to the power supply and to the sensor.

10. The device of claim 9 where the control unit determines by look-up-table or transfer function an output value of physical quantity and where the input power is regulated based on the value determined by look-up-table or transfer function.

11. The device of claim 9 where the control unit calculates output power of the electrode.

12. A method for contactless skin treatment by electromagnetic waves, comprising:
provclaim high frequency power from a high frequency generator to an electrode;
transmitting electromagnetic waves from the electrode into skin of a patient, with the electrode not touching the skin of the patient;
measuring a distance between the electrode and the skin of the patient; and
adjusting input power to the high frequency generator based on the measured distance to provide continuous energy to the skin of the patient via feedback power control.

13. The method of claim 12 further including measuring temperature.

14. The method of claim 13 wherein skin temperature during treatment is maintained between 38° C.-48° C.

15. The method of claim 12 further including measuring impedance.

16. The method of claim 12 further including matching impedance between the high frequency generator and the electrode via a transmatch.

17. The method of claim 12 further including measuring electric field intensity.

18. The method of claim 12 wherein the electromagnetic waves cause heating of the skin.

19. The method of claim 18 wherein the heating causes remodeling and/or downsizing of a volume of lipid-rich cells and/or remodeling of collagen tissue and/or remodeling of elastic fibers.

20. The method of claim 12 further including calculating a true transmitted energy.

21. The method of claim 12 further including gradually increasing the input power.

22. A method for contactless skin treatment by electromagnetic waves, comprising:
providing high frequency power from a high frequency generator to at least two electrodes;
matching impedance between the high frequency generator and the at least two electrodes via a transmatch;
transmitting electromagnetic waves from the at least two electrodes into skin of a patient, with the electrodes not touching the skin of the patient, and with the electromagnetic waves heating the skin;
measuring values of at least one physical quantity between different branches of first and second symmetrical signal cables leading to the at least two electrodes;
adjusting input power to the high frequency generator based on the at least one physical quantity; and
providing energy to the skin of the patient via the adjusted input power to the high frequency generator.

23. The method of claim 22 wherein the at least one physical quantity is at least one of: temperature, distance between the electrode and the skin of the patient, impedance, electric field intensity, current, voltage, phase shift.

24. The method of claim 22 further including calculating a true transmitted energy.

25. The method of claim 22 further including gradually increasing the input power.

26. The method of claim 25 further including reducing the input power if the sensed physical quantity exceeds a threshold.

* * * * *